United States Patent [19]

Walker

[11] Patent Number: 5,001,136
[45] Date of Patent: Mar. 19, 1991

[54] LEUKOTRIENE-SYNTHESIS-INHIBITING 2-SUBSTITUTEDMETHYLAMINO-5-(HYDROXY OR ALKOXY)PYRIDINES

[75] Inventor: Frederick J. Walker, Preston, Conn.

[73] Assignee: Pfizer Inc., New York, N.Y.

[21] Appl. No.: 534,789

[22] Filed: Jun. 7, 1990

[51] Int. Cl.$^5$ .................. A61K 31/44; C07D 213/74; C07D 405/12
[52] U.S. Cl. .................. 514/336; 514/349; 546/297; 546/283; 546/284
[58] Field of Search .................. 546/297, 283, 284; 514/336, 349

[56] References Cited

U.S. PATENT DOCUMENTS 4,038,396 7/1977 Shen et al. .................. 424/256

OTHER PUBLICATIONS

Watnick et al., *Arch Pol. Pharmaeodyn* 190, 78–90 (1971).
Nantha et al., *Acta Pol. Pharm.* 33(1), 7–11 (1976).
Moore et al., *J. Org. Chem.* 32, 1353–1360 (1966).
Moore et al., *J. Org. Chem.* 30, 1887–1889 (1964).
Lombardino et al., *J. Med. Chem.* 24, 39–42 (1981).
Hayakawa et al., *Chem. Pharm. Bull.* 32, 4914 (1984).
Klingsberg, E., "Pyridine and its Derivatives, Part Three", Interscience Publishers, 1962, pp. 8–9, 560–565.
Jakschick et al., *Prostoglandins* 16, 733–747 (1978).
Sherlock et al., *J. Med. Chem.* 31(11), 2108–2111 (1988).
Chang et al., *Biochemistry* 26(2), 360–367 (1987).
Crank et al., *J. Heterocycl. Chem.* 22(5), 1281–1284 (1985).

*Primary Examiner*—Robert W. Ramsuer
*Assistant Examiner*—Michael G. Ambrose
*Attorney, Agent, or Firm*—Peter C. Richardson; Paul H. Ginsburg; Karen DeBenedictis

[57] ABSTRACT

2-substitutedmethylamino-amino 5-(hydroxy or alkoxy) pyridines and derivatives thereof are disclosed. The compounds are inhibitors of leukotriene synthesis and are therefore useful for the treatment of pulmonary, inflammatory, dermatological, allergic and cardiovascular diseases.

9 Claims, No Drawings

LEUKOTRIENE-SYNTHESIS-INHIBITING 2-SUBSTITUTEDMETHYLAMINO-5-(HYDROXY OR ALKOXY)PYRIDINES

BACKGROUND OF THE INVENTION

This invention relates to hydroxy and alkoxy substituted pyridines, more particularly, to 2-substituted amino 5-(hydroxy or alkoxy) pyridines and acyl derivatives thereof. The compounds of this invention are inhibitors of leukotriene syntheses and are therefore useful in the treatment of pulmonary, inflammatory, dermatological, allergic and cardiovascular diseases.

Watnick et al., Arch. Int. Pharmaeodyn., 190, 78–90 (1971), refer to the anti-inflammatory and analgesic properties of clonixin (2-(2'-methyl-3'-chloroanilino) nicotinic acid).

Nantha et al., Acta Pol. Pharm., 33(1), 7–11(1976), refer to certain derivatives of 2-anilino-5-hydroxynicotinic acid, including 6-methyl-2-anilino-5-hydroxynicotinic acid.

Shen et al., in U.S. Pat. No. 4,038,396, refer to the anti-inflammatory properties of certain oxazolo[4,5-b]pyridines.

Moore et al., J. Org. Chem., 32, 1353–1360 (1966) refer to the production of certain 2-carbonylamino-3-phenyl-4-methyl-5-hydroxy pyridines by heating unsaturated acyldiazabicyclic ketones in methanol.

Moore et al., J. Org. Chem., 30, 1887–9 (1964), refer to the production of 2-methylamino-3-phenyl-4-methyl-5-hydroxy pyridine by heating 2,5-dimethyl-4-phenyl-2,3-dihydro-6H-diazapin-6-one in a base.

Lombardino et al., J. Med. Chem., 24, 39–42 (1981), refers to 2-amino-5-methoxy pyridine as an intermediate in the synthesis of certain metabolites of the anti-inflammatory agent piroxicam.

Current treatment of asthma focuses on the relief of acute bronchospasm through the use of bronchodilators. It is thought that acute bronchospasm is only an overt manifestation of chronic inflammation. Leukotrienes may play a role both in the bronchospasm and the chronic inflammation. They are known to be potent vasodilators and chemotactic agents. They are also produced in allergic reactions and bring about slow contraction of lung tissue in vitro. An inhibitor of leukotriene synthesis should therefore be of use in the treatment of asthma and other pulmonary diseases.

Chronic gastric and duodenal ulcers, together known as peptic ulcers, are the subject of a variety of treatments, including special diets, drug therapy and surgery, depending upon the severity of the condition. Particularly valuable therapeutic agents useful for the treatment of gastric hyperacidity and peptic ulcers are the histamine-$H_2$ receptor antagonists, which block the action of the physiologically-active compound histamine at the $H_2$-receptor sites in the animal body and thereby inhibit the secretion of gastric acid.

SUMMARY OF THE INVENTION

The present invention relates to compounds of the formula

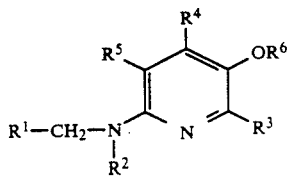

wherein $R^1$ is $(C_1-C_{15})$alkyl, $(C_1-C_{15})$alkyl-$(C_3-C_8)$cycloalkyl, $(C_2-C_{15})$alkenyl - $(C_3-C_8)$cycloalkenyl, $(C_2-C_{15})$alkynyl - $(C_3-C_8)$cycloalkyl, $(C_3-C_{15})$-alkynyl, a heteroaryl contain selected from heteroaryl - $(C_1-C_{10})$alkyl, heteroaryl -$(C_1-C_{10})$ alkenyl, and heteroaryl -$(C_1-C_{10})$alkynyl, wherein the heteroaryl moiety is selected from the group consisting of thienyl and furyl; $(C_7-C_{20})$phenylalkyl, substituted $(C_7-C_{20})$phenylalkyl, $(C_7-C_{20})$phenylalkenyl, substituted $(C_7-C_{20})$-phenylalkenyl, $(C_7-C_{20})$phenylalkynyl, substituted $(C_7-C_{20})$phenylalkynyl, $(C_1-C_6$ alkoxy$)$ - $(C_2-C_6)$ alkyl, phenoxy - $(C_2-C_6)$alkyl, substituted phenoxy -$(C_2-C_6)$alkyl, $(C_1-C_6)$alkoxy- $(C_2-C_6)$alkenyl, $(C_1-C_6)$alkoxy -$(C_2-C_6)$alkynyl, phenoxy -$(C_2-C_6)$alkenyl, substituted phenoxy- $(C_2-C_6)$alkenyl, phenoxy -$(C_2-C_6)$-alkynyl, substituted phenoxy- $(C_2-C_6)$alkynyl, or $(C_7-C_{12})$phenylalkyl- $(C_7-C_{12})$phenylalkyl, wherein the phenyl moieties of said substituted $(C_7-C_{20})$ phenylalkyl, substituted $(C_7-C_{20})$ phenylalkenyl, substituted $(C_7-C_{20})$ phenylalkynyl, substituted phenoxy- $(C_2-C_6)$alkyl, substituted phenoxy- $(C_2-C_6)$alkenyl, and substituted phenoxy -$(C_2-C_6)$alkynyl are substituted with one to two substitutuents independently selected from chloro, fluoro, bromo, $(C_1-C_4)$alkoxy, $(C_1-C_4)$alkyl and trifluoromethyl; $R^2$ is hydrogen; $R^3$ is hydrogen, $(C_1-C_6)$alkyl, phenyl, substituted phenyl, benzyl and substituted benzyl, wherein said substituted phenyl and the phenyl moiety of said substituted benzyl are substituted with from one to two substituents independently selected from chloro, fluoro, bromo, $(C_1-C_4)$alkoxy, $(C_1-C_4)$alkyl and trifluoromethane; $R^4$ is hydrogen or $(C_1-C_6)$alkyl; $R^5$ is phenyl, substituted phenyl, or hydrogen, wherein said substituted phenyl is substituted with one to two substituents independently selected from chloro, fluoro, bromo, $(C_1-C_4)$alkoxy, $(C_1-C_4)$alkyl and trifluoromethane; $R^6$ is —COR , hydrogen or $(C_1-C_7)$alkyl; $R^7$ is hydrogen or $(C_1-C_4)$ alkyl; with the proviso that when $R^4$ is methyl, $R^3$ is hydrogen and $R^5$ is phenyl, then $R^1$ cannot be methyl; and the pharmaceutically acceptable salts of such compounds.

This invention includes all stereoisomers of the compounds of the formula I.

A preferred embodiment of the present invention relates to compounds of formula I wherein $R_1$ is $(C_1-C_{15})$-alkyl, $(C_7-C_{20})$phenylalkyl, or substituted $(C_7-C_{20})$-phenylalkyl, wherein the phenyl moieties of said substituted phenyl and said substituted phenylalkyl may be substituted by one to two substituents independently selected from the group consisting of chloro and $(C_1-C_3)$alkyl; $R^3$ is $(C_1-C_6)$alkyl or phenyl optionally substituted with one to two substituents independently selected from the group consisting of fluoro, chloro, methyl, ethyl, methoxy, ethoxy, and $CF_3$; and $R^4$ is hydrogen or $(C_1-C_6)$alkyl.

Another preferred embodiment of the present invention relates to compounds of the formula I wherein $R^2$ is hydrogen; $R^1$ is $(C_7-C_{12})$phenylalkyl which may be substituted in the phenyl moiety by one or two substituents independently selected from the group consisting of fluoro, chloro, ($C_1$–$C_3$)alkyl, ($C_1$–$C_3$)alkoxy, and trifluoromethyl; and $R^3$ and $R^4$ are each hydrogen.

A particularly preferred embodiment of the present invention relates to compounds of the formula I wherein $R^2$ is hydrogen; $R^1$ is ($C_8$–$C_9$)alkyl, ($C_9$–$C_{12}$)-phenylalkyl, or ($C_9$–$C_{12}$)p-chlorophenylalkyl; and $R^3$ and $R^4$ are each hydrogen.

Examples of preferred compounds of the present invention are 2-(3-p-chlorophenyl-n-propyl)amino-5-hydroxypyridine and 2-(5-phenyl-n-pentyl)amino-5-hydroxy The term "alkyl", as used herein, denotes saturated, monovalent, straight or branched aliphatic hydrocarbon radicals such as methyl, ethyl, propyl, butyl, t-butyl, hexyl, octyl, 2-ethylhexyl, etc.

The term "alkenyl", as used herein, denotes monovalent straight or branched hydrocarbon radicals containing one carbon-carbon double bond and being otherwise saturated, such as ethenyl, propenyl, 1-butenyl, t-butenyl, 2-hexenyl, 2-ethyl-4-hexenyl, etc.

The term "alkynyl", as used herein, denotes straight or branched hydrocarbon radicals containing one carbon-carbon triple bond and being otherwise saturated, such as acetylenyl, propynyl, 1-butynyl, 2-hexynyl, 2-ethyl-4-hexynyl, etc.

The term "phenylalkyl", as used herein, denotes a phenyl group attached to saturated straight or branched aliphatic hydrocarbon radicals. Examples of such phenylalkyls are phenylmethyl, phenylethyl, phenylpropyl, phenylbutyl, phenylpentyl, phenylhexyl, phenyloctyl, 1,1-dimethyl-7-phenylheptyl etc.

The term "phenylalkenyl", as used herein, denotes a phenyl group attached to straight or branched aliphatic hydrocarbon radicals containing one carbon-carbon double bond and being otherwise saturated. Examples of phenylalkenyls are 1-phenyl-1-butenyl, 1-phenyl-1-pentenyl, 1-phenyl-3-hexenyl, etc.

The term "phenylalkynyl", as used herein, denotes a phenyl group attached to straight or branched aliphatic hydrocarbon radicals containing one carbon-carbon triple bond and being otherwise saturated. Examples of phenylalkynyls are 1-phenyl-1-butynyl, 1-phenyl-1-pentynyl, 1-phenyl-3-hexynyl, etc.

The present invention also relates to a method of inhibiting leukotriene synthesis in a mammal, including a human, comprising administering to said mammal a leukotriene synthesis inhibiting effective amount of a compound of the formula I, or a pharmaceutically acceptable acid or base addition salt thereof.

The present invention also relates to a method of treating a pulmonary, asthmatic, dermatologic, cardiovascular, allergic or inflammatory disease in a mammal, including a human, comprising administering to a mammal in need of such treatment a leukotriene synthesis inhibiting effective amount of a compound of the formula I, or a pharmaceutically acceptable acid or base addition salt thereof.

The present invention also relates to a method of treating a disease selected from asthma, arthritis, bronchitis, hypertension, hypoxia, peptic ulcers, psoriasis, inflammatory bowel disease, cardiovascular spasm, and acute myocardial infarctions in a mammal, comprising administering to said mammal, including a human, a leukotriene synthesis inhibiting effective amount of a compound of the formula I, or a pharmaceutically acceptable acid or base addition salt thereof.

The present invention also relates to a pharmaceutical composition comprising a leukotriene synthesis inhibiting effective amount of a compound of the formula I, or a pharmaceutically acceptable acid or base addition salt thereof, and a pharmaceutically acceptable carrier.

DETAILED DESCRIPTION OF THE INVENTION

The following reaction scheme illustrates the preparation of compounds of the formula I. Unless otherwise indicated, in the reaction scheme and discussion that follows, $R^1$, $R^2$, $R^3$, $R^4$, $R^5$, $R^6$, and $R^7$, are defined as above.

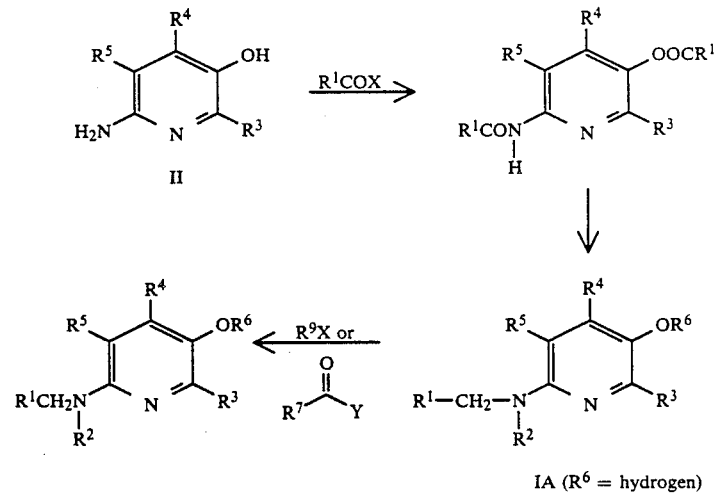

A compound of the formula II is reacted with an acid halide of the formula $R_1COX$, wherein X is halogen, preferably chlorine, to form a compound of formula III. This reaction is generally carried out at a temperature from about −20° C. to about room temperature, preferably at about 0° C., for at least 15 minutes. The reaction time will vary with the temperature. The reaction may be speeded up by heating the reaction mixture after addition of all of the halide to about 20° to about 30° C., e.g. 25° C., for at least about 15 minutes, usually for about 0.5 hour. Polar aprotic solvents may be used. Preferred solvents include methylene chloride, tetrahydrofuran, ether, and chloroform.

Compounds of formula I wherein $R^6$ is hydrogen (represented in the reaction scheme by structure IA), may be formed by reacting the corresponding compound of formula III with a hydride reducing agent. Suitable hydride reducing agents include diisobutylaluminum hydride and sodium bis(2-methoxyethoxy)aluminum hydride. Diisobutylaluminum hydride is preferred. The reaction is generally carried out at a temperature from about $-78°$ to about $-10°$ C., preferably at about $-23°$ C. Suitable solvents include dry inert solvents such as tetrahydrofuran, ether, toluene and benzene. The preferred solvent is tetrahydrofuran.

Compounds of formula I wherein $R^6$ is $(C_1-C_4)$alkyl may be formed by reacting the corresponding compounds of the formula I wherein $R^6$ is hydrogen with a compound of the formula $R^9X$, wherein X is a group which easily reacts with the hydroxyl group of the compound of the formula I, e.g., a chloro, bromo, tosyl or mesyl, and $R^9$ is $(C_1-C_4)$ alkyl. When $R_6$ is methyl, methylating agents such as dimethylsulfate may be used as well.

This reaction is generally carried out in a dry inert atmosphere such as nitrogen or argon under anhydrous conditions in an aprotic, polar solvent. Examples of such solvents are tetrahydrofuran, dimethylformamide, and dimethylsulfoxide. Dimethylformamide is preferred. Suitable reaction temperatures range from about $0°$ to about $100°$ C., preferably from about $25°$ to about $30°$ C. The reaction is facilitated by forming the phenolate salt of the compounds of the formula I by conducting the reaction in the presence of a base. Organic bases such as triethylamine and inorganic bases such as sodium hydroxide and potassium hydroxide may be used.

Compounds of the formula I wherein $R^6$ is $—COR^7$ may be prepared by acylating the corresponding compounds of the formula IA with an acylating agent. The acylating agent may be an active ester, for example, an acetic anhydride, or an acid chloride. For example, the acylating agent may be a compound of the formula

wherein Y is chlorine or bromine.

This reaction is generally carried out in a reaction inert solvent in the presence of a base, under a dry inert atmosphere such as dry nitrogen or dry argon. Examples of solvents that may be used are methylene chloride and ether. Examples of suitable bases are triethylamine and pyridine. Alternatively, a base such as pyridine may be used as the solvent. The reaction is usually maintained at a temperature from about $-20°$ to about $50°$ C., preferably at about $0°$ C., for about 0.5 to about 24 hours, preferably for about 2 hours.

The acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. Examples of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic such as methanesulfonic, benzensulfonic, and related acids. Preferably, the acid is phosphoric acid.

The base addition salts of the compounds of formula I, wherein $R_6$ is hydrogen, may be prepared in a conventional manner by reacting such compounds of the formula I with about one chemical equivalent of an inorganic base such as an alkali metal hydroxide or an alkaline earth metal hydroxide.

Compounds of the formula II may be prepared by literature methods or by methods known to those skilled in the art. (See, e.g., Pyridine and its Derivatives, Part Three, Erwin Klingsberg, Ed., Interscience Publishers, pp 8–9, 560–565 (1962); Moore, J.A. et al., *J Org. Chem*, 30, 1887 (1965); Hayakawa, I. et al., *Chem. Pharm. Bull.*, 32, 4914 (1984); Moore, J.A. et al., *J. Am. Chem. Soc.*, 81, 6049 (1959)).

In each of the reactions discussed or illustrated above, pressure is not critical unless otherwise indicated. Pressures from about 0.5 atmospheres to about 5.0 atmospheres are generally acceptable, and ambient pressure, i.e. about one atmosphere, is preferred as a matter of convenience.

The compounds of formula I and their pharmaceutically acceptable acid addition salts are inhibitors of leukotriene synthesis and agents for the treatment of various pulmonary, gastrointestinal, allergic, inflammatory, dermatological and cardiovascular conditions. In particular, the compounds have utility, both as the sole active agent and also in combination with other active agents, for the treatment of mammals, including humans, affected with asthma, bronchitis, pulmonary diseases such as pulmonary hypertension and hypoxia, peptic ulcers, psoriasis, arthritis, inflammatory bowel disease and cardiovascular spasm such as acute myocardial infarctions.

For treatment of the various conditions described above, the compounds of formula I may be administered to a subject in need of treatment by a variety of conventional routes of administration, including oral, by injection, topical, and in an aerosol carrier composition for administration by breathing or topical application.

In general, a therapeutically-effective dose for the active compounds of formula I will range from about 0.01 to about 100 mg/kg body weight of the subject to be treated per day, preferably from about 0.1 to about 50 mg/kg per day.

Although the compounds of formula I can be administered alone, they will generally be administered in admixture with a pharmaceutical carrier selected with regard to the intended route of administration and standard pharmaceutical practice. For example, for oral administration, they may be in the form of tablets containing such excipients as starch or lactose, in capsules either alone or in admixture with excipients, or in the form of elixirs or suspensions containing flavoring or coloring agents. In the case of animals, they are advantageously contained in animal feed or drinking water. For parenteral injection, they may be used in the form of a sterile aqueous solution which may contain other solutes, for example enough salt or glucose to make the solution isotonic. For topical use, they may be formulated in solutions, suspensions, gels, creams, or ointments, such formulations preferably including one or more excipients to prevent or retard decomposition, such as ascorbic acid, sodium bisulfite, or dithiothreitol, and agents to adjust the pH, such as sodium hydroxide, hydrochloric acid or sodium bicarbonate.

The activity of the compounds of formula I in the treatment of pulmonary (e.g., asthmatic), allergic, dermatological (e.g., psoriasis) and inflammatory diseases may be determined by a standard test measuring an agent's ability to inhibit cyclooxygenase and lypoxygenase enzyme activity of rat basophil leukemia (RBL-1) cells. According to this test as described by Jakschick et al., *Prostaglandins*, 16,733-747 (1978), a monolayer of RBL-1 cells is grown for 1 or 2 days in spinner culture in Eagle's minimum essential medium, 15% heat-inactivated fetal calf serum and an antibiotic/antimycotic mixture. The cells are washed after centrifugation and incubated in a buffer. A volume of 0.5 ml of cell suspension is preincubated at 30° C. for ten minutes with a 1 microliter dimethylsulfoxide (DMSO) solution of the agent to be tested. The incubation is initiated by simultaneous addition of 5 microliters of ($^{14}$C)—arachidonic acid in ethanol and 2 microliters of calcium ionophore (A-21387) in DMSO for final concentrations of 5 and 7.6M, respectively. Five minutes later, the incubation is terminated by the addition of 0.27 ml acetonitrile/acetic acid (100:3). Thin layer chromatography is performed using acetonitrile/water/acetic acid solvent.

The following Examples illustrate but do not limit the scope of this invention. All melting points referred to in the Examples are uncorrected.

EXAMPLE 1

2-(3-p-Chlorophenyl-n-propyl)amino-5-hydroxypyridine 1.56 Grams (3.65 millimoles) of 2-(3-p-chloro-phenyl-n-propyl) amido-5-(3-p-chlorophenyl-n-propanoyl)-oxypyridine in a dry nitrogen atmosphere was dissolved in 25 milliliters dry tetrahydrofuran, cooled to −23° C., and treated with 14.6 milliliters of 1 molar diisobutylaluminum hydride in hexanes. The reaction mixture was stirred and allowed to stand at room temperature for 18 hours. The reaction was then quenched with 100 milliliters of saturated ammonium hydroxide, filtered and washed with 100 milliliters of ethyl acetate. The layers were separated and the aqueous layer was extracted several times with 100 milliliters of ethyl acetate. The combined organics were dried, filtered and concentrated. The residue was purified by chromatography on silica gel (120 g) eluting with ethyl acetate/hexanes in a 3:2 ratio. There was obtained 0.68 grams (71 percent) of a yellow solid m.p.: 95°-97° C. NMR (CDCl$_3$) delta 7.7 (d, 1 H), 7.3-6.9 (m, 5 H), 6.3 (d, 1 H), 3.2 (t, 2 H), 2.6 (t, 2 H), 1.9 (q, 2 H). IR (CHCl$_3$) 3581, 2932, 1615, 1580, 1485 cm$^{-1}$. M.S. 262 (p). Anal. calc'd for C$_{14}$H$_{15}$N$_2$OCl: C, 64.00; H, 5.75; N, 10.66. Found: C, 63.45; H, 5.73; N, 10.42.

EXAMPLE 2

2-(3-p-Chlorophenyl-n-propyl)amido-5-(3-p-chorophenyl-n-propanoyl) oxypyridine 1.42 Grams (1.29 milliliters) of 2-amino-5hydroxypyridine in 10 milliliters pyridine in a dry nitrogen atmosphere at 0° C. was treated with 3-p-chlorophenyl-n-propanoyl chloride in tetrohydrofuran, such solution having been prepared from 5.72 grams (3.02 millimoles) of 3-p-chlorophenyl-n-propanoic acid and thionyl chloride, and stirred for 1.5 hours. The reaction mixture was concentrated and the residue was taken up in ethyl acetate. The organics were washed three times with brine, once with water, and then dried and concentrated. Chromatography on 240 grams silica gel eluting with ethyl acetate/hexanes in a ratio of 1:1 afforded 1.56 grams (28 percent) of a yellow solid. NMR (CDCl$_3$) delta 8.5 (bs, 1 H), 8.4 (bs, 1 H), 8.3 (bs, 1 H), 8.0 (bs, 1 H), 7.6-7.03 (m, 8 H), 3.3-2.43 (m, 8 H).

EXAMPLE 3

2-(5-Phenyl-n-pentyl)amino-5-hydroxypyridine 1.56 Grams (3.62 millimoles) 2-(5-phenyl-n-pentyl) amido-5-(5-phenylpentanoyl)oxypyridine in a dry nitrogen atmosphere was dissolved in 25 milliliters dry tetrahydrofuran, cooled to −23° C., and treated with 10.9 milliliters (10.9 millimoles) of 1 molar diisobutyl aluminum hydride in hexanes. The reaction mixture was quenched with 25 milliliters ammonium hydroxide and allowed to stand at room temperature for 18 hours. The reaction mixture was then diluted with 50 milliliters water and ethyl acetate and filtered. After washing with 100 milliliters of ethyl acetate, the organic layer was separated and washed two times with 50 milliliters of water and once with 25 mililiters of brine. The dried organics were filtered and concentrated. Chromatography on 120 grams silica gel eluting with ethyl acetate/hexanes in a ratio of 7:3 afforded 0.21 grams of a yellow solid, m.p.: 79°-81° C. NMR (CDCl$_3$) delta 8.0-7.6 (m, 1 H), 7.4-7.0 (m, 7 H), 6.3 (d, 1 H), 3.2 (t, 2 H), 2.6 (t, 2 H), 2.0-1.2 (m, 6 H). IR (CHCl$_3$) 3590, 3420, 1620, 1590, 1480 cm$^{-1}$. M.S. 256 (p) Anal.: Calc'd for C$_{16}$H$_{20}$N$_2$O: C, 74.97, H, 7.86, N, 10.93. Found: C, 74.46, H, 7.81, N, 10.93.

EXAMPLE 4

2-(5-Phenyl-n-pentyl)amido-5-(5-phenylpentanoyl)-oxypyridine 0.9 Grams (8.17 millimoles) 2-amino-5-hydroxypyridine was dissolved in 25 milliliters of pyridine, cooled to 0° C. and treated with 5-phenylpentanoyl chloride (19.1 millimoles) in methylene chloride (0.5 ml) prepared from 3.41 grams (19.1 millimoles) 5-phenylpentanoic acid and thionyl chloride. The reaction was stirred for 18 hours and allowed to come to room temperature. The reaction was concentrated and the residue was dissolved in ethyl acetate and water. The layers were separated and the organics were washed two times with water, two times with brine, and dried, filtered and concentrated. Chromatography on 2.40 grams silica gel eluting with ethyl acetate/hexanes in a ratio of 1:3 afforded 1.56 grams (44 percent) of a solid. NMR (CDCl$_3$) delta 8.3-8.0 (m, 4 H), 7.5-7.0 (m, 10 H), 2.9-2.2 (m, 8 H), 2.0-1.4 (m, 8 H). M.S. 430 (p).

I claim:

1. A compound of the formula

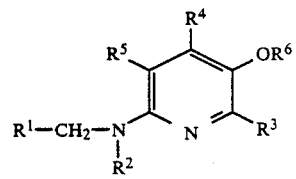

wherein R$^1$ is (C$_1$-C$_{15}$)alkyl, (C$_1$-C$_{15}$)alkyl-(C$_3$-C$_8$)cycloalkyl, (C$_2$-C$_{15}$)alkenyl - (C$_3$-C$_8$)cycloalkenyl, (C$_2$-C15)alkynyl - (C$_3$-C$_8$)cycloalkyl, (C$_3$-C$_{15}$)alkynyl, a heteroaryl containing group selected from heteroaryl - (C$_1$-C$_{10}$)alkyl, heteroaryl -(C$_1$-C$_{10}$) alkenyl, and heteroaryl - (C$_1$-C$_{10}$)alkynyl, wherein the heteroaryl moiety is selected from thienyl and furyl; (C$_7$-C$_{20}$)

phenylalkyl, substituted (C$_7$–C$_{20}$) phenylalkyl, (C$_7$–C$_{20}$)phenylalkenyl, substituted (C$_7$–C$_{20}$) phenylalkenyl, (C$_7$–C$_{20}$)phenylalkynyl, substituted (C$_7$–C$_{20}$) phenylalkynyl, (C$_1$–C$_6$)alkoxy - (C$_2$–C$_6$)alkyl, phenoxy - (C$_2$–C$_6$)alkyl, substituted phenoxy -(2–C$_6$)alkyl, (C$_1$–C$_6$)alkoxy- (C$_2$–C$_6$)alkenyl, substituted phenoxy-(C$_2$–C$_6$)alkenyl, phenoxy -(C$_2$–C$_6$)-alkenyl, substituted phenoxy- (C$_2$–C$_6$)alkynyl, or C$_7$–C$_{12}$)-phenylalkyl-(C$_7$–C$_{12}$) phenylalkyl; wherein the phenyl moieties of said substituted (C$_7$–C$_{20}$) phenylalkyl, substituted (C$_7$–C$_{20}$) phenylalkenyl, substituted (C$_7$–C$_{20}$) phenylalkynyl, substituted phenoxy- (C$_2$–C$_6$)-alkyl, substituted phenoxy- (C$_2$–C$_6$)alkenyl, and substituted phenoxy -(C$_2$–C$_6$)alkynyl are substituted with one to two substitutuents independently selected from chloro, fluoro, bromo, (C$_1$–C$_4$)alkyl, (C$_1$–C$_4$)alkoxy and trifluromethyl; R$^2$ is hydrogen; R$^3$ is hydrogen, (C$_1$–C$_6$)alkyl, phenyl, substituted phenyl, benzyl and substituted benzyl, wherein the phenyl moieties of said substituted phenyl and substituted benzyl may optionally be substituted with one to two substitutuents independently selected from chloro, fluoro, bromo, (C$_1$–C$_4$)alkyl, (C$_1$–C$_4$)alkoxy and trifluoromethyl; R$^4$ is hydrogen or (C$_1$–C$_6$)alkyl; R$^5$ is hydrogen or phenyl, wherein said phenyl may optionally be substituted with one to two substituents independently selected from chloro, fluoro, bromo, (C$_1$–C$_4$)alkyl, (C$_1$–C$_4$)alkoxy and trifluoromethyl; R$^6$ is —COR$^7$, hydrogen or (C$_1$–C$_7$)alkyl; and R$^7$ is hydrogen or (C$_1$–C$_4$)alkyl; with the proviso that when R$^4$ is methyl, R$^3$ is hydrogen and R$^5$ is phenyl, then R$^1$ is not methyl;

or a pharmaceutically acceptable salt of such compound.

2. A compound according to claim 1, wherein R$_1$ is (C$_1$–C$_{15}$)alkyl, (C$_7$–C$_{20}$)phenylalkyl wherein the phenyl moiety of said (C$_7$–C$_{20}$) phenylalkyl may optionally be substituted w one or two substituents independently selected from chloro and (C$_1$–C$_3$)alkyl; R$^3$ is (C$_1$–C$_6$)alkyl or phenyl optionally substituted with one or two substituents independently selected from fluoro, chloro, methyl, ethyl, methoxy, ethoxy, and trifluoromethyl; and R$^4$ is (C$_1$–C$_6$)alkyl.

3. A compound according to claim 1, wherein R$^1$ is (C$_7$–C$_{12}$)phenylalkyl wherein the phenyl moiety is optionally substituted with one or two substituents independently selected from fluoro, chloro, (C$_1$–C$_3$)-alkyl, (C$_1$–C$_3$)alkoxy and trifluoromethyl; and R$^3$ and R$^4$ are each hydrogen.

4. A compound according to claim 1, wherein R$^1$ is (C$_8$–C$_9$)alkyl, (C$_9$–C$_{12}$)phenylalkyl, or (C$_9$–C$_{12}$)-p-chlorophenylalkyl, and R$^3$ and R$^4$ are each hydrogen.

5. A compound according to claim 1, wherein said compound is 2-(3-p-chlorophenyl-n-propyl)amino-5-hydroxypyridine or 2-(5-phenyl-n-pentyl)amino-5-hydroxypyridine.

6. A pharmaceutical composition comprising a leukotriene synthesis inhibiting effective amount of a compound according to claim 1 and a pharmaceutically acceptable carrier.

7. A method of inhibiting leukotriene synthesis in a mammal, comprising administering to said mammal a leukotriene synthesis inhibiting effective amount of a compound according to claim 1.

8. A method of treating a pulmonary, asthmatic, dermatologic, cardiovascular, allergic or inflammatory disease in a mammal, comprising administering to a mammal in need of such treatment a leukotriene synthesis inhibiting effective amount of a compound according to claim 1.

9. A method of treating a disease selected from asthma, arthritis, bronchitis, hypertension, hypoxia, peptic ulcers, psoriasis, inflammatory bowel disease, cardiovascular spasm, and acute myocardial infarctions in a mammal, comprising administering to said mammal a leukotriene synthesis inhibiting effective amount of a compound according to claim 1.

* * * * *